US011103428B2

(12) United States Patent
Ho

(10) Patent No.: US 11,103,428 B2
(45) Date of Patent: Aug. 31, 2021

(54) SURFACTANT FREE SILICONE EMULSION

(71) Applicant: NuSil Technology LLC, Carpinteria, CA (US)

(72) Inventor: Ricky Siu-Kei Ho, Carpinteria, CA (US)

(73) Assignee: NuSil Technology LLC, Carpinteria, CA (US)

( * ) Notice: Subject to any disclaimer, the term of this patent is extended or adjusted under 35 U.S.C. 154(b) by 0 days.

(21) Appl. No.: 16/093,434

(22) PCT Filed: Apr. 11, 2017

(86) PCT No.: PCT/US2017/026918
§ 371 (c)(1),
(2) Date: Oct. 12, 2018

(87) PCT Pub. No.: WO2017/180567
PCT Pub. Date: Oct. 19, 2017

(65) Prior Publication Data
US 2019/0209447 A1 Jul. 11, 2019

Related U.S. Application Data

(60) Provisional application No. 62/323,088, filed on Apr. 15, 2016.

(51) Int. Cl.
| | |
|---|---|
| *A61K 8/06* | (2006.01) |
| *A61K 8/04* | (2006.01) |
| *A61K 8/81* | (2006.01) |
| *A61K 8/892* | (2006.01) |
| *A61Q 17/04* | (2006.01) |
| *A61Q 19/08* | (2006.01) |
| *C08L 83/04* | (2006.01) |
| *C08J 3/03* | (2006.01) |
| *A61Q 19/00* | (2006.01) |
| *C08G 77/16* | (2006.01) |

(52) U.S. Cl.
CPC .............. *A61K 8/062* (2013.01); *A61K 8/042* (2013.01); *A61K 8/8147* (2013.01); *A61K 8/892* (2013.01); *A61Q 17/04* (2013.01); *A61Q 19/00* (2013.01); *A61Q 19/08* (2013.01); *C08J 3/03* (2013.01); *C08L 83/04* (2013.01); *A61K 2800/31* (2013.01); *A61K 2800/33* (2013.01); *A61K 2800/5424* (2013.01); *C08G 77/16* (2013.01); *C08J 2383/04* (2013.01)

(58) Field of Classification Search
CPC ................ A61K 8/062; A61K 2800/33; A61K 2800/31; A61K 8/8147; A61K 8/892; C08L 83/04; C08G 77/16
See application file for complete search history.

(56) References Cited

U.S. PATENT DOCUMENTS

| | | | | |
|---|---|---|---|---|
| 5,073,371 | A * | 12/1991 | Turner | A61Q 19/008 424/401 |
| 5,637,291 | A * | 6/1997 | Bara | A61Q 19/00 424/59 |
| 2007/0292380 | A1* | 12/2007 | Staudigel | A61K 8/892 424/70.13 |
| 2008/0287336 | A1 | 11/2008 | Patel et al. | |
| 2011/0150806 | A1* | 6/2011 | Bui | A61K 8/8111 424/70.7 |
| 2013/0064777 | A1 | 3/2013 | Tamarkin et al. | |
| 2014/0242016 | A1 | 8/2014 | Binks et al. | |
| 2015/0196481 | A1 | 7/2015 | Mitra et al. | |
| 2015/0196570 | A1 | 7/2015 | Tamarkin et al. | |
| 2016/0101051 | A1 | 4/2016 | Tamarkin et al. | |

FOREIGN PATENT DOCUMENTS

| | | | | |
|---|---|---|---|---|
| WO | WO-02092047 A1 * | 11/2002 | | A61Q 19/00 |

OTHER PUBLICATIONS

PCT Search Report and Written Opinion Application No. PCT/US17/26918 dated Jul. 17, 2017.

* cited by examiner

*Primary Examiner* — Jianfeng Song
(74) *Attorney, Agent, or Firm* — Hoffmann & Baron, LLP

(57) ABSTRACT

A silicone emulsion free of a surfactant and an emulsifier is disclosed. The emulsion includes a dispersed oil phase having a polyorganosiloxane with one or more hydroxyl groups in a continuous aqueous or anhydrous organic diol phase including an anionic polymer.

14 Claims, No Drawings

SURFACTANT FREE SILICONE EMULSION

RELATED APPLICATIONS

This application is the U.S. National Phase of, and Applicant claims priority from, International Patent Application No. PCT/US2017/026918, filed on Apr. 11, 2017, which claims benefit of U.S. Provisional Application No. 62/323,088, entitled "OIL-IN-WATER SURFACTANT FREE SILICONE EMULSION," filed on Apr. 15, 2016, each of which are herein incorporated by reference in their entireties.

TECHNICAL FIELD

The present invention relates to silicone emulsions that can be used in cosmetic, dermatologic, personal care, healthcare, aerospace and household applications. More specifically, it relates to a stable system of silicone emulsion which can be made without the use of surfactants and/or emulsifiers to form the emulsions.

BACKGROUND

Traditional oil-in-water emulsions have been prepared by adding emulsifiers or surfactants in order to maintain the dispersion of small droplets in the internal phase during emulsification. Emulsifiers have an amphiphilic molecular structure with a hydrophilic head and hydrophobic tail which are separated from one another. Emulsifiers lower the interfacial tension between the phases and form an interfacial film to prevent irreversible coalescence of the droplets. If the interfacial tension is too high, the droplet will not be stable in the medium and the interfacial phase will break down due to high free energy. If the interfacial tension is too low, the droplet will easily rupture and lead to coalescence.

There is a negative impact of emulsifiers or surfactants on some of the users associated with skin irritation due to a modification of the stratum corneum multilamellar lipid structure. Emulsifiers or surfactants can penetrate through the skin barrier and act as lipid solvents. When water is present on the skin, the skin lipids can wash away with the emulsifiers or surfactants and reduce the skin barrier defense systems.

In consideration of the above, a new way to create a stable emulsion without negative impact on the skin is needed.

SUMMARY OF THE DISCLOSURE

An advantage of the present disclosure is silicone emulsion that is stable without the use of a surfactant or emulsifier.

These and other advantages are satisfied, at least in part, by a silicone emulsion comprising: a dispersed oil phase comprising a polyorganosiloxane having one or more hydroxyl groups in a continuous phase comprising an aqueous or organic diol medium including an anionic polymer. Advantageously, the silicone emulsion is free of a surfactant or an emulsifier.

Embodiments of the present disclosure include wherein the polyorganosiloxane having one or more hydroxyl groups is a hydroxyl terminated or hydroxyalkyl terminated polyorganosiloxane, the anionic polymer is an anionic polymer having carboxyl groups, e.g., a polyacrylic acid polymer. In some embodiments, the oil phase can further include one or more other polyorganosiloxane, an oil containing silicon atoms, organic based oil, hydrocarbon based oil, etc. The oil phase can further include other hydrophobic ingredients. In other embodiments, the emulsion can include other ingredients either in the oil phase or aqueous phase including one or more active agents, fragrances, perfumes, plant extracts, flavoring agent, powders, and/or preservatives.

Another aspect of the present disclosure includes a variety of compositions that includes the emulsions of the present disclosure, e.g., compositions as cosmetic, dermatologic, personal care, healthcare, household compositions. For example, an aspect of the present disclosure includes topical cosmetic compositions that include the emulsions of the present disclosure. Such compositions can be applied to the skin with a translucent or transparent appearance which comes from the aqueous gel formed in the medium or gel containing glycerin, propylene glycol, butylene glycol and methylpropanediol.

Embodiments of such compositions include any type of active ingredient (e.g., vitamins, plant extract, proteins, etc.) or non-active agent (e.g., powders, microspheres, etc.).

Another advantage of the present disclosure is a method of preparing a stable silicone emulsion without the use of a surfactant or emulsifier. The method comprises dispersing an oil including a hydroxyl-containing polyorganosiloxane and is free of a surfactant or an emulsifier in an aqueous or organic diol medium containing an anionic polymer and free of a surfactant or an emulsifier to form the silicone emulsion free of a surfactant or emulsifier.

Embodiments include any one or more of the features described for the emulsion of the present disclosure, individually or combined. In addition, embodiments of the present disclosure include wherein dispersing the oil in aqueous medium includes neutralizing the aqueous medium with a neutralizer, e.g., an alkalizing agent such as sodium hydroxide.

Additional advantages of the present invention will become readily apparent to those skilled in this art from the following detailed description, wherein only the preferred embodiment of the invention is shown and described, simply by way of illustration of the best mode contemplated of carrying out the invention. As will be realized, the invention is capable of other and different embodiments, and its several details are capable of modifications in various obvious respects, all without departing from the invention. Accordingly, the description is to be regarded as illustrative in nature, and not as restrictive.

DETAILED DESCRIPTION OF THE DISCLOSURE

The present disclosure relates to a silicone emulsion in which an oil phase is dispersed in a continuous aqueous or organic diol phase. In accordance with aspects of the present disclosure, the oil phase includes a polyorganosiloxane having one or more hydroxyl groups and the aqueous or organic diol medium includes an anionic polymer.

Advantageously, the emulsions of the present disclosure are stable without the use of a surfactant or an emulsifier. It is believed that the stability of the emulsions of the present disclosure is achieved by hydrogen bonding interactions and steric stabilization between hydroxyl-containing polyorganosiloxane and the anionic polymer in the aqueous or organic diol medium. As used herein a stable emulsion means one that does not demonstrate substantial coalescence or a substantial change in the average size of micelles for at least 12 months under ambient conditions as determined by optical microscopy. Advantageously, the emulsions of the present invention do not demonstrate substantial change in appearance or change in rheological properties for at least 12 months under ambient conditions as well.

The phrase free of a compound or compound free as used herein means that the emulsion of the present disclosure includes no more than a trace amount of the compound as an impurity e.g., no more than about 0.001 mol/L such as low as 0.0001 mol/L. That is, a silicone emulsion free of a surfactant or an emulsifier includes no more than a trace amount of the surfactant or the emulsifier as an impurity e.g., no more than about 0.0001 mol/L of either the surfactant or the emulsifier.

The types of surfactants and emulsifiers that the emulsion can be free of include ammonium laureth sulfatate, cetalkonium chloride, DEA myristate, docyl polyglucose, dioctyl sodium sulfosuccinate, disodium cocoamphodiacetate, disodium laurimino dipropionate, luaryl betaine, luaryl pyrrolidone, nonoxynol-12, myristamine oxide, PEG-50 stearate, potassium dodecylbenzenesulfonate, potassium oleate, sodium cocoyl glutamate, sodium $C_{14-16}$ olefin sulfonate, sodium laureth phosphate, sodium lauryl sulfate, sodium methyl oleoyl taurate, sodium nonoxynol-25 sulfate, sodium oleoyl isethionate, sodium stearate, TEA-abietoyl hydrolyzed collagen, TEA-lauryl sulfate, TEA-oleoyl sarcosinate, ceteareth-10, Cetrimonium bromide, laneth-5, lecithin, nonoxynol-9, PEG-20 dilaurate, PEG-8 oleate, poloxamer 407, polyglyceryl-8 oleate, polysorbate 60, sorbitan sequioleate, sucrose stearate, cocamine oxide, lauramide DEA, myristamide MIPA, myristaminopropionic acid, ammonium xylenesulfonate, potassium toluenesulfonate, sodium methyl naphthalene sulfonate, cetareth-40, oleth-44, PEG-40 stearate, behentrimonium chloride, benzethonium chloride, sodium lignosulfonate, sodium polystyrene sulfonate. In an embodiment of the present disclosure, a silicone emulsion comprises a dispersed oil phase comprising a polyorganosiloxane having one or more hydroxyl groups in a continuous phase comprising an aqueous or organic diol medium including an anionic polymer, wherein the silicone emulsion is free of a surfactant or an emulsifier, including the foregoing surfactants and emulsifiers.

Advantageously, the emulsion can also be prepared without addition of amine functional polymers or surface treated fillers where the surface treatment of the filler serves to stabilize an emulsion. In an embodiment, the emulsions of the present disclosure can also be free of amine functionalized polyorganosiloxance, e.g., amine functionalized methicone or dimethicone, such as amodimethicone).

In the present disclosure, the one or more hydroxyl groups of the polyorganosiloxane are necessary to stabilize the emulsion. In addition, a linear and/or branched polyorganosiloxane with hydroxyl groups is believed to create steric stabilization and hydrogen bonding interactions with the anion polymer in the aqueous phase. A suitable polyorganosiloxane must contain hydroxyl groups at the end of the chain and/or pendant to the chain. Chain lengths having a degree of polymerization (DP) of at least 3000 DP are preferred, with 6500 DP more preferred.

Useful polyorganosiloxane having one or more hydroxyl groups include a linear, or branched polyorganosiloxanes having one or more hydroxyl groups. Such a polyorganosiloxane can be represented by the following formula (I):

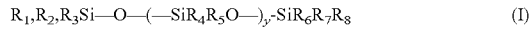

$$R_1,R_2,R_3Si-O-(-SiR_4R_5O-)_y-SiR_6R_7R_8 \quad (I)$$

wherein y is an integer of from about 1,000 to about 3000, e.g., 6,500 or more and each of $R_1$ to $R_8$ are individually a substituted or unsubstituted $C_{1-8}$ alkyl or aryl, provided at least one of $R_1$ to $R_8$ is a hydroxyl group or a $C_{1-8}$ alkyl or aryl substituted with a hydroxyl group, that is any one or more of $R_1$ to $R_8$ is a hydroxyl, a hydroxyl substituted $C_{1-8}$ alkyl or a hydroxyl substituted $C_{1-8}$ aryl substituted. The $C_{1-8}$ alkyl or aryl groups can be substituted with one or more halogens, e.g., by F or Cl. For example, the repeating unit can be any one of dimethylsiloxane, dimethyldiphenylsiloxane, dimethyltrifluoropropylmethylsiloxane, dimethylmethylhydrogensiloxane, provided at least one repeating unit or an end unit includes a hydroxyl group. In an embodiment of the present disclosure, one or more of $R_1$, $R_2$, $R_3$, $R_6$, $R_7$, $R_8$, is a hydroxyl or a hydroxyl substituted $C_{1-8}$ alkyl, e.g., a hydroxyl terminated or hydroxyalkyl terminated polyorganosiloxane. In another embodiment of the present disclosure, the polyorganosiloxane having one or more hydroxyl groups is a dimethiconol.

The oil phase can further include one or more other polyorganosiloxane, an oil containing silicon atoms, organic based oil, hydrocarbon based oil, etc. The oil phase can further include other hydrophobic ingredients such one or more active agents.

For example, polyorganosiloxane without hydroxyl groups can be included in the oil phase based on the nature of solubility and/or dispersability of any types of fluid or combination of fluid and filler such as natural oil, wax, gum, diluted elastomer, powder or paste. The oil phase can also include other polyorganosiloxane such as linear, branched or cyclic siloxanes. Additional polyorganosiloxanes that can be included in the oil phase disclosure include: monomethylsiloxane, trimethylsiloxane, methylvinylsiloxane, methylethylsiloxane, diethylsiloxane, methylphenylsiloxane, diphenylsiloxane, ethylphenylsiloxane, vinylethylsiloxane, phenylvinylsiloxane, 3,3,3-trifluoropropylmethylsiloxane, dimethyldiphenylsiloxane, dimethylphenylsiloxane, methylphenylvinylsiloxane, dimethylethylsiloxane, 3,3,3-trifluoropropylmethyldimethylsiloxane, mono-3,3,3-trifluoropropylsiloxane, polyethyleneglycol and/or polypropyleneglycol methylsiloxanes, polyethyleneglycol and/or polypropyleneglycol phenylsiloxanes, polyethyleneglycol and/or polypropyleneglycol alkylsiloxanes polyethyleneglycol and/or polypropyleneglycol 3,3,3-trifluoropropylmethylsiloxanes, C3-C60 alkyl methylsiloxanes, C3-C60 alkylphenylsiloxanes, aminoalkylsiloxane, diaminoalkylsiloxane, monophenylsiloxane, monovinylsiloxane and other combinations.

It is believed that the stability of the emulsions of the present disclosure is achieved by hydrogen bonding interactions and steric stabilization between hydroxyl-containing polyorganosiloxane and the anionic polymer in the aqueous or organic diol medium. A disperse oil phase of an emulsion of the present disclosure including other polyorganosiloxane, the other polyorganosiloxanes are stabilized by a protective layer thus created. The interaction of opposite charges and/or dipole-dipole interaction from the interphase stabilizes the aqueous or organic diol and oil phases within the emulsion.

Useful anionic polymers included in the aqueous or organic diol phase of the emulsions of the present disclosure include polymers with functionality capable of yielding a proton such as polymers containing carboxylic acid groups e.g., —COOH. Such polymers form carboxylic anions, e.g., —COO⁻ when the pH of the aqueous or organic diol medium is above the pKa value of the carboxylic acid which can be achieved with neutralizing agents, e.g., alkaline agents such as sodium hydroxide. Similar anionic groups also can be found with linear or branched polymers made from acrylic acid, maleic acid, and other monomers e.g., acrylamide, alkyl acrylates, $C_5$-$C_8$ alkyl acrylates, C10-C30 alkyl acrylates, C12-C22 alkyl methacrylates, methoxypolyethyleneglycol methacrylates, hydroxyl ester acrylates. In an embodiment of the present disclosure, an anionic polymer is a polyacrylic acid (PAA), e.g., a carbomer.

Another aspect of the present disclosure includes preparing a stable silicone emulsion. The method comprises dispersing an oil including a hydroxyl-containing polyorganosiloxane and is free of a surfactant or an emulsifier in an aqueous or organic diol medium containing an anionic polymer and free of a surfactant or an emulsifier to form the silicone emulsion free of a surfactant or emulsifier. In some embodiments, the emulsion is formed by changes of condition in the aqueous or organic diol medium (temperature, pH, electrolytes, concentration of reagents, etc). For example, in preparing the emulsion, the aqueous or organic diol medium can be neutralized, e.g., the pH of the aqueous phase can be adjusted to form the anionic polymer, if needed such as by increasing the pH with a neutralizing agent. The aqueous or organic diol medium can be neutralized either before, during or after forming the dispersion of the oil phase in the aqueous or organic diol medium.

Neutralizing agent or neutralizers that can be used with emulsions of the present disclosure include compounds that can increase the pH of the aqueous or organic diol medium, e.g., compounds considered alkaline such as alkali metal hydroxides, i.e., sodium hydroxide, amines, i.e., triethanolamine, potassium hydroxide, as well as ammonium hydroxide, arginine, aminomethylpropanol, tetrahydroxypropyl ethylenediamine, tromethamine, PEG-15 Cocamine, diisopropanolamine, triisopropanolamine, etc.

In one embodiment of practicing the present disclosure, an oil including a hydroxyl-containing polyorganosiloxane is mixed with an aqueous or organic diol medium including the anionic polymer and a neutralizing agent is added to form the emulsion. For example, such a process generally involves preparing a first formulation with a polymer containing caboxylic groups in an aqueous or organic diol medium and preparing a second formulation with a polyorganosiloxane having one or more hydroxyl groups typically with other polyorganosiloxanes. The emulsion is generally formed by changes of condition in the medium (temperature, pH, electrolytes, concentration of reagents, etc). In one example, the stabilization of the interphase network is achieved by the neutralization of the carboxylic group with sodium hydroxide or a solution thereof to form carboxylate in the first formulation and the interaction of the hydroxyl from the second formulation. This interphase network isolates the aqueous phase from the oil phase. The interphase network is flexible enough to self-heal to some degree.

In one aspect of the present disclosure, a stable emulsion comprising one or more polyorganosiloxanes, e.g., one or more polyorganosiloxanes with dimethylsiloxne units, diphenylsiloxane units, trifluoropropylsiloxane units, ethylene oxide/dimethylsiloxane combinations and the structure based on any fluid and crosslinked polymer, is formed by the interphase network between the carboxylate and hydroxyl groups within the aqueous and oil phases, e.g, carbomer and an hydroxyl functional polyorganosiloxane. The hydroxyl functional polyorganosiloxane alone or combination with any crosspolymer can be dispersed in an aqueous or organic diol medium or gel. In one embodiment the percentage of the oil phase (polyorganosiloxane with or without any additional ingredients such as actives or particles) can be from about 1% to 70% of the overall concentration with a typical concentration between 30-50%. The average size of the oil droplet is less than 400 μm. The amount of polymer with the carboxylic groups can be about 0.01% to about 10%.

The emulsion of the present disclosure can have a wide range of viscosities, e.g., greater than about 10,000 centipoise (cP), such as greater than 50,000 cP, 100,000 cP or 200,000 cP. In an embodiment of the present disclosure, the emulsion viscosity can be relatively high from 20,000 cP, 50,000 cP, or greater than 100,000 cp.

Another aspect of the present disclosure includes a variety of compositions that includes the emulsions of the present disclosure, e.g., compositions as cosmetic, dermatologic, personal care, healthcare, household compositions. For example, an aspect of the present disclosure includes topical cosmetic compositions that include the emulsions of the present disclosure. Such compositions can be applied to the skin with a translucent or transparent appearance which comes from the aqueous gel formed in the medium or gel containing glycerin, propylene glycol, butylene glycol and methylpropanediol.

The emulsion of the present disclosure can be used as an ingredient in any type of topical composition with an opaque to transparent appearance. In addition, other hydrophilic ingredients are easily dispersed in the aqueous phase and mixed with the oil phase before and/or after the neutralization. This type of emulsion can be utilized in any type of personal care, healthcare or aerospace applications such as but not limited to serums, lotions, creams, pastes, liquid to powder, powders, cleansers and soaps, rinses, sprays, shampoos, conditioners, lacquers, balms, glosses, pomades, fixatives, dressings, lubricants, shaving aids and foams, dyes, bleaches, oils, gels, masks, patches or thin-film coating and de-icing.

A surfactant free emulsion is advantageous since surfactants have been linked to skin irritation. In this surfactant free system, the polyorganosiloxane from the oil phase can be dispersed with other hydrophobic ingredients before or after incorporation into an aqueous phase without the use of surfactants.

In the present disclosure, an emulsion can be formed with varied appearances, textures and sensory aspects with changes in the composition from the oil phase and/or water phase. This flexibility allows the emulsion to form an opaque to transparent appearance for any applications in the cosmetic industry. Further advantages include the ability to increase or decrease the amount of the polyorganosiloxane to create thinner or thicker film on the skin.

The emulsion of the present disclosure also allows for the alteration of texture, appearance and sensory feel that cannot be replicated with the same amount of polyorganosiloxane in other suspension or emulsion systems.

Other advantages of the present disclosure include the controlled delivery of a drug or active ingredient. In addition, ingredients that can be incorporated include one or more synthetic or natural oils dispersed or suspended in the oil phase.

The emulsion of the present disclosure can include other ingredients either in the oil phase or aqueous phase including one or more active agents, fragrances, perfumes, plant extracts, flavoring agent, powders, and/or preservatives.

The oil phase can include hydrophobic ingredient such as organic or hydrocarbon based oils. Oils containing silicon atoms, or blends of organic oils and oils contain silicon atoms can be also incorporated in the oil phase of the emulsion. Such oils include coconut oil; hydrocarbons such as mineral oil and hydrogenated polyisobutene; fatty alcohols such as octyldodecanol; esters such as C12-C15 alkyl benzoate; diesters such as propylene dipelarganatedipelargonate; and triesters, such as glyceryl trioctanoate. The organic oil components can also be mixtures of oils of differing viscosities. Examples of low viscosity oils include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate, octododecanoloctyldodecanol, or mixtures of octyldodecanol, acetylated lanolin alcohol, cetyl acetate, isododecanol, polyglyceryl-3-diisostearate, or mixtures thereof. The high viscosity oils can include castor oil, lanolin and lanolin derivatives, triisocetyl citrate, sorbitan sesquioleate, C10-18 triglycerides, caprylic/capric/triglycerides, coconut oil, corn oil, cottonseed oil, glyceryl triacetyl hydroxystearate, glyceryl triacetyl ricinoleate, glyceryl trioctanoate, hydrogenated castor oil, linseed oil, mink oil, olive oil, palm oil, rapeseed oil, soybean oil, sunflower seed oil, tallow, tricaprin, trihydroxystearin, triisostearin, trilaurin, trilinolein, trimyristin, triolein, tripalmitin, tristearin, walnut oil, wheat germ oil, cholesterol, or mixtures thereof. Mention may be made, among the optional other non-silicone fatty substances, of mineral oils, such as liquid paraffin or liquid petroleum, of animal oils, such as perhydrosqualene or arara oil, or alternatively of vegetable oils, such as sweet almond, calophyllum, palm, castor, avocado, jojoba, olive or cereal germ oil. It is also possible to use esters of lanolic acid, of oleic acid, of lauric acid, of stearic acid or of myristic acid, for example; alcohols, such as oleyl alcohol, linoleyl or linolenyl alcohol, isostearyl alcohol or octyldodecanol; or acetylglycerides, octanoates, decanoates or ricinoleates of alcohols or of polyalcohols.

One or more active ingredients can be included in the oil phase with the hydroxyl containing polyorganosiloxane or in the aqueous or organic diol phase. Such active ingredients can be used for personal care, healthcare, and pharmaceuticals formulations. An active in personal care or skin care is mainly for cosmetic, aesthetic, protective or sensory benefit. An active in healthcare is mainly to provide a pharmaceutical or medical benefit. Another purpose of actives can be for pharmacological activity or any other functions such as diagnosis, cure, mitigation, treatment, prevention or to affect any function of the body in human or other animals.

Active agents can include vitamins, derivatives or pro-vitamins. Such vitamins, derivatives or pro-vitamins include Vitamin A1, retinol, $C_2$-$C_{18}$ esters of retinol, vitamin E, tocopherol, esters of vitamin E, and mixtures thereof. Retinol includes trans-retinol, 1,3-cis-retinol, 11-cis-retinol, 9-cis-retinol, and 3,4-didehydro-retinol, Vitamin C and its derivatives, Vitamin B1, Vitamin B2, Pro Vitamin B5, panthenol, Vitamin B6, Vitamin B12, niacin, folic acid, biotin, and pantothenic acid. Other suitable vitamins and the INCI names for the vitamins considered included herein are ascorbyl dipalmitate, ascorbyl methylsilanol pectinate, ascorbyl palmitate, ascorbyl stearate, ascorbyl glucocide, sodium ascorbyl phosphate, sodium ascorbate, disodium ascorbyl sulfate, potassium (ascorbyl/tocopheryl) phosphate.

Active agents can include any water soluble or oil soluble pharmaceutical active. Such pharmaceutical actives include hydrocortisone, ketoprofen, timolol, pilocarpine, adriamycin, mitomycin C, morphine, hydromorphone, diltiazem, theophylline, doxorubicin, daunorubicin, heparin, penicillin G, carbenicillin, cephalothin, cefoxitin, cefotaxime, 5-fluorouracil, cytarabine, 6-azauridine, 6-thioguanine, vinblastine, vincristine, bleomycin sulfate, aurothioglucose, suramin, mebendazole clonidine, scopolamine, propranolol, phenylpropanolamine hydrochloride, ouabain, atropine, haloperidol, isosorbide, nitroglycerin, ibuprofen, ubiquinones, indomethacin, prostaglandins, naproxen, salbutamol, guanabenz, labetalol, pheniramine, metrifonate, and steroids.

Another example of active ingredients can be proteins or enzymes. The benefit of an oil phase with a self-healing interphase network is its action as a protective barrier for any potential degradation of protein or enzyme. Suitable enzymes include commercially available types, improved types, recombinant types, wild types, variants not found in nature, and mixtures thereof. For example, suitable enzymes include hydrolases, cutinases, oxidases, transferases, reductases, hemicellulases, esterases, isomerases, pectinases, lactases, peroxidases, laccases, catalases, and mixtures thereof. Hydrolases include, but are not limited to, proteases (bacterial, fungal, acid, neutral or alkaline), amylases (alpha or beta), lipases, mannanases, cellulases, collagenases, lisozymes, superoxide dismutase, catalase, and mixtures thereof. Said protease include, but are not limited to, trypsin, chymotrypsin, pepsin, pancreatin and other mammalian enzymes; papain, bromelain and other botanical enzymes; subtilisin, epidermin, nisin, naringinase (L-rhammnosidase) urokinase and other bacterial enzymes. Said lipase include, but are not limited to, triacyl-glycerol lipases, monoacyl-glycerol lipases, lipoprotein lipases, e.g. steapsin, erepsin, pepsin, other mammalian, botanical, bacterial lipases and purified ones. Natural papain is preferred as said enzyme. Further, stimulating hormones, e.g. insulin, can be used together with these enzymes to boost the effectiveness of them.

The active agent can also be an organic, inorganic or a mixture of sunscreen ingredients. The sunscreen ingredients can be used to protect the skin from harmful UV rays from sunlight. In most cases, the sunscreen ingredients will reflect or absorb the UVA and UVB rays from sunlight. For example, suitable sunscreen ingredients include, but are not limited to, Aminobenzoic Acid, Cinoxate, Diethanolamine Methoxycinnamate, Digalloyl Trioleate, Dioxybenzone, Ethyl 4-[bis(Hydroxypropyl)] Aminobenzoate, Glyceryl Aminobenzoate, Homosalate, Lawsone with Dihydroxyacetone, Menthyl Anthranilate, Octocrylene, Octyl Methoxycinnamate, Octyl Salicylate, Oxybenzone, Padimate O, Phenylbenzimidazole Sulfonic Acid, Red Petrolatum, Sulisobenzone, Titanium Dioxide, and Trolamine Salicylate, cetaminosalol, Allatoin PABA, Benzalphthalide, Benzophenone, Benzophenone 1-12, 3-Benzylidene Camphor, Benzylidenecamphor Hydrolyzed Collagen Sulfonamide, Benzylidene Camphor Sulfonic Acid, Benzyl Salicylate, Bornelone, Bumetriozole, Butyl Methoxydibenzoylmethane, Butyl PABA, Ceria/Silica, Ceria/Silica Talc, Cinoxate, DEA-Methoxycinnamate, Dibenzoxazol Naphthalene, Di-t-Butyl Hydroxybenzylidene Camphor, Digalloyl Trioleate, Diisopropyl Methyl Cinnamate, Dimethyl PABA Ethyl Cetearyldimonium Tosylate, Dioctyl Butamido Triazone, Diphenyl Carbomethoxy Acetoxy Naphthopyran, Disodium Bisethylphenyl Tiamminotriazine Stilbenedisulfonate, Disodium Distyrylbiphenyl Triaminotriazine Stilbenedisulfonate, Disodium Distyrylbiphenyl Disulfonate, Drometrizole, Drometrizole Trisiloxane, Ethyl Dihydroxypropyl PABA, Ethyl Diisopropylcinnamate, Ethyl Methoxycinnamate, Ethyl PABA, Ethyl Urocanate, Etrocrylene Ferulic Acid, Glyceryl Octanoate Dimethoxycinnamate, Glyceryl PABA, Glycol Salicylate, Homosalate, Isoamyl p-Methoxycinnamate, Isopropylbenzyl Salicylate, Isopropyl Dibenzolylmethane, Isopropyl Methoxycinnamate, Menthyl Anthranilate, Menthyl Salicylate, 4-Methylbenzylidene, Camphor, Octocrylene, Octrizole, Octyl Dimethyl PABA, Octyl Methoxycinnamate, Octyl Salicylate, Octyl Triazone, PABA, PEG-25 PABA, Pentyl Dimethyl PABA, Phenylbenzimidazole Sulfonic Acid, Polyacrylamidomethyl Benzylidene Camphor, Potassium Methoxycinnamate, Potassium Phenylbenzimidazole Sulfonate, Red Petrolatum, Sodium Phenylbenzimidazole Sulfonate, Sodium Urocanate, TEA-Phenylbenzimidazole Sulfonate, TEA-Salicylate, Terephthalylidene Dicamphor Sulfonic Acid, Titanium Dioxide, Zinc Dioxide, Serium Dioxide, TriPABA Panthenol, Urocanic Acid, and VA/Crotonates/Methacryloxybenzophenone-1 Copolymer. One or combination of more than one of these sunscreen agents can be selected. Alternatively, the sunscreen agent can be a cinnamate based organic compound, or alternatively, the sunscreen agent can be octyl methoxycinnamate, such as Parsol MCX or Uvinul® MC 80 an ester of para-methoxycinnamic acid and 2-ethylhexanol.

Other compounds that can be included within the emulsion of the present disclosure are fragrances or perfume. Most of the fragrances or perfumes typically belong to a variety of chemicals such as alcohols, aldehydes, ketones, esters, ethers, acetates, nitrites, terpenic hydrocarbons, heterocyclic nitrogen or sulfur containing compounds, as well as essential oils of natural or synthetic origin. For example, suitable fragrances or perfumes include, but are not limited to, buccoxime; iso jasmone; methyl beta naphthyl ketone; musk indanone; tonalid/musk plus; Alpha-Damascone, Beta-Damascone, Delta-Damascone, Iso-Damascone, Damascenone, Damarose, Methyl-Dihydrojasmonate, Menthone, Carvone, Camphor, Fenchone, Alpha-lonone, Beta-lonone, Gamma-Methyl so-called Ionone, Fleuramone, Dihydrojasmone, Cis-Jasmone, Iso-E-Super, Methyl-Cedrenyl-ketone or Methyl-Cedrylone, Acetophenone, Methyl-Acetophenone, Para-Methoxy-Acetophenone, Methyl-Beta-Naphtyl-Ketone, Benzyl-Acetone, Benzophenone, Para-Hydroxy-Phenyl-Butanone, Celery Ketone or Livescone, 6-Isopropyldecahydro-2-naphtone, Dimethyl-Octenone, Freskomenthe, 4-(1-Ethoxyvinyl)-3,3,5,5,-tetramethyl-Cyclohexanone, Methyl-Heptenone, 2-(2-(4-Methyl-3-cyclohexen-1-yl)propyl)-cyclopentan one, 1-(p-Menthen-6(2)-yl)-1-propanone, 4-(4-Hydroxy-3-methoxyphenyl)-2-butanone, 2-Acetyl-3,3-Dimethyl-Norbomane, 6,7-Dihydro-1,1,2,3,3-Pentamethyl-4(5H)-Indanone, 4-Damascol, Dulcinyl or Cassione, Gelsone, Hexalon, Isocyclemone E, Methyl Cyclocitrone, Methyl-Lavender-Ketone, Orivon, Para-tertiary-Butyl-Cyclohexanone, Verdone, Delphone, Muscone, Neobutenone, Plicatone, Veloutone, 2,4,4,7-Tetramethyl-oct-6-en-3-one, and Tetrameran. Preferably, the perfume aldehyde is selected for its odor character from adoxal; anisic aldehyde; cymal; ethyl vanillin; florhydral; helional; heliotropin; hydroxycitronellal; koavone; lauric aldehyde; lyral; methyl nonyl acetaldehyde; P. T. bucinal; phenyl acetaldehyde; undecylenic aldehyde; vanillin; 2,6,10-trimethyl-9-undecenal, 3-dodecen-1-al, alpha-n-amyl cinnamic aldehyde, 4-methoxybenzaldehyde, benzaldehyde, 3-(4-tert butylphenyl)-propanal, 2-methyl-3-(para-methoxyphenyl propanal, 2-methyl-4-(2,6,6-trimethyl-2(1)-cyclohexen-1-yl) butanal, 3-phenyl-2-propenal, cis-/trans-3,7-dimethyl-2,6-octadien-1-al, 3,7-dimethyl-6-octen-1-al, [(3,7-dimethyl-6-octenyl)oxy] acetaldehyde, 4-isopropylbenzaldehyde, 1,2,3,4,5,6,7,8-octahydro-8,8-dimethy]-2-naphthaldehyde, 2,4-dimethyl-3-cyclohexen-1-carboxaldehyde, 2-methyl-3-(isopropylphenyl)propanal, 1-decanal; decyl aldehyde, 2,6-dimethyl-5-heptanal, 4-(tricyclo[5.2.1.0(2,6))-decylidene-8)-butanal, octahydro-4,7-methano-1H-indenecarboxaldehyde, 3-ethoxy-4-hydroxy benzaldehyde, para-ethyl-alpha, alpha-di methyl hydrocinnamaldehyde, alpha-methyl-3,4-(methylenedioxy)-hydrocinnamaldehyde, 3,4-methylenedioxybenzaldehyde, alpha-n-hexyl cinnamic aldehyde, m-cymene-7-carboxaldehyde, alpha-methyl phenyl acetaldehyde, 7-hydroxy-3,7-dimethyl octanal, Undecenal, 2,4,6-trimethyl -3-cyclohexene-1-carboxaldehyde, 4-(3)(4-methyl-3-pentenyl)-3-cyclohexencarboxaldehyde, 1-dodecanal, 2,4-dimethyl cyclohexene-3-carboxaldehyde, 4-(4-hydroxy4-methyl pentyl)-3-cylohexene-1-carboxaldehyde, 7-methoxy-3,7-dimethyloctan-1-al, 2-methyl undecanal, 2-methyl decanal, 1-nonanal, 1-octanal, 2,6,10-trimethyl-5,9-undecadienal, 2-methyl-3-(4-tertbutyl)propanal, dihydrocinnamic aldehyde, 1-methyl-4-(4-methyl-3-pentenyl)-3-cyclohexene-1-carboxaldehyde, 5 or 6 methoxyl 0 Hexahydro-4,7-methanoindan-1 or 2-carboxaldehyde, 3,7-dimethyloctan-1-al, 1-undecanal, 10-undecen-1-al, 4-hydroxy-3-methoxy benzaldehyde, 1-methyl-3-(4-methylpentyl)-3-cyclhexenecarboxaldehyde, 7-hydroxy-3,7-dimethyl-octanal, trans-4-decenal, 2,6-nonadienal, paratolylacetaldehyde; 4-methylphenylacetaldehyde, 2-methyl-4-(2,6,6-trimethyl-1-cyclohexen-1-yl)-2-butenal, ortho-methoxycinnamic aldehyde, 3,5,6-trimethyl-3-cyclohexene carboxaldehyde, 3,7-dimethyl-2-methylene-6-octenal, phenoxyacetaldehyde, 5,9-dimethyl-4,8-decadienal, peony aldehyde (6,10-dimethyl-3-oxa-5,9-undecadien-1-al), hexahydro-4,7-methanoindan-1-carboxaldehyde, 2-methyl octanal, alpha-methyl-4-(1-methyl ethyl) benzene acetaldehyde, 6,6-dimethyl-2-norpinene-2-propionaldehyde, para methyl phenoxy acetaldehyde, 2-methyl-3-phenyl-2-propen-1-al, 3,5,5-trimethyl hexanal, Hexahydro-8,8-dimethyl-2-naphthaldehyde, 3-propyl-bicyclo[2.2.1]-hept-5-ene-2-carbaldehyde, 9-decenal, 3-methyl-5-phenyl-1-pentanal, methylnonyl acetaldehyde, hexanal, trans-2-hexenal, 1-p-menthene-q-carboxaldehyde and mixtures thereof.

For certain applications, the emulsion can include a plant extract. Plant extracts include, but are not limited to Ashitaba extract, avocado extract, *hydrangea* extract, Althea extract, *Arnica* extract, aloe extract, apricot extract, apricot kernel extract, *Ginkgo Biloba* extract, fennel extract, turmeric[*Curcuma*] extract, oolong tea extract, rose fruit extract, *Echinacea* extract, Scutellaria root extract, Phellodendro bark extract, Japanese Coptis extract, Barley extract, Hyperium extract, White Nettle extract, Watercress extract, Orange extract, Dehydrated saltwater, seaweed extract, hydrolyzed elastin, hydrolyzed wheat powder, hydrolyzed silk, Chamomile extract, Carrot extract, *Artemisia* extract, *Glycyrrhiza* extract, hibiscustea extract, Pyracantha Fortuneana Fruit extract, Kiwi extract, Cinchona extract, cucumber extract, guanocine, *Gardenia* extract, Sasa Albo-*marginata* extract, *Sophora* root extract, Walnut extract, Grapefruit extract, *Clematis* extract, *Chlorella* extract, mulberry extract, *Gentiana* extract, black tea extract, yeast extract, burdock extract, rice bran ferment extract, rice germ oil, comfrey extract, collagen, cowberry extract, *Gardenia* extract, Asiasarum Root extract, Family of Bupleurum extract, umbilical cord extract, *Salvia* extract, *Saponaria* extract, Bamboo extract, *Crataegus* fruit extract, Zanthoxylum fruit extract, shiitake extract, Rehmannia root extract, gromwell extract, *Perilla* extract, linden extract, Filipendula extract, peony extract, Calamus Root extract, white birch extract, Horsetail extract, *Hedera Helix*(Ivy) extract, hawthorn extract, *Sambucus nigra* extract, *Achillea millefolium* extract, *Mentha piperita* extract, sage extract, mallow extract, Cnidium *officinale* Root extract, Japanese green gentian extract, soybean extract, jujube extract, thyme extract, tea extract, clove extract, Gramineae *imperata* cyrillo extract, Citrus unshiu peel extract Japanese Angelica Root extract, Calendula extract, Peach Kernel extract, Bitter orange peel extract, Houttuyna *cordata* extract, tomato extract, natto extract, *Ginseng* extract, Green tea extract (camellica sinesis), grape seed extract, garlic extract, wild rose extract, hibiscus extract, Ophiopogon tuber extarct, *Nelumbo nucifera* extract, parsley extract, honey, *hamamelis* extract, *Parietaria* extract, Isodonis herba extract, bisabolol extract, Loquat extract, coltsfoot extract, butterbur extract, Porid *cocos* wolf extract, extract of butcher's broom, grape extract, propolis extract, luffa extract, safflower extract, peppermint extract, linden tree extract, *Paeonia* extract, hop extract, pine tree extract, horse chestnut extract, Mizubashou [Lysichiton camtschatcese]extract, Mukurossi peel extract, Melissa extract, peach extract, cornflower extract, *eucalyptus* extract, saxifrage extract, citron extract, *coix* extract, mugwort extract, lavender extract, apple extract, lettuce extract, lemon extract, Chinese milk vetch extract, rose extract, rosemary extract, Roman Chamomile extract, and royal jelly extract.

A flavoring agent can also be included such as oil of wintergreen; peppermint oil; spearmint oil; menthol; vanilla; cinnamon oil; clove oil; bay oil; anise oil; *eucalyptus* oil; thyme oil; cedar leaf oil; oil of nutmeg; oil of sage; *cassia* oil; cocoa; licorice; high fructose corn syrup; citrus oils such as lemon, orange, lime, and grapefruit; fruit essences such as apple, pear, peach, grape, strawberry, raspberry, cherry, plum, pineapple, and apricot; and other useful flavoring agents including aldehydes and esters such as cinnamyl acetate, cinnamaldehyde, eugenyl formate, p-methylanisole, acetaldehyde, benzaldehyde, anisic aldehyde, citral, neral, decanal, vanillin, tolyl aldehyde, 2,6-dimethyloctanal, and 2-ethyl butyraldehyde.

Powders can be added with the present disclosure for cosmetic and health effect. A typical effect includes, but is not limited to any type of color agent such as pigments, dyes, inks, or active agents to generate a specific color or powders/microspheres to alter the light scattering on the skin. Typical pigments such as $TiO_2$, ZnO and treated pigments, pigment masterbatches or dispersions. In general, the particle size of the powders can range from 0.02 to 200 microns but it is preferred from 0.5 to 100 micron with color or non-color (for example white). Such powders include bismuth oxychloride, titanated mica, fumed silica, spherical silica, polymethylmethacrylate, micronized teflon, boron nitride, acrylate polymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium carbonate, magnesium hydroxide, magnesium oxide, magnesium silicate, magnesium trisilicate, maltodextrin, montmorillonite, microcrystalline cellulose, rice starch, silica, talc, mica, titanium dioxide, zinc laurate, zinc myristate, zinc neodecanoate, zinc rosinate, zinc stearate, polyethylene, alumina, attapulgite, calcium carbonate, calcium silicate, dextran, kaolin, nylon, silica silylate, silk powder, sericite, soy flour, tin oxide, titanium hydroxide, trimagnesium phosphate, walnut shell powder, or mixtures thereof. The above mentioned powders may be surface treated with lecithin, amino acids, mineral oil, silicone oil, or various other agents either alone or in combination, which coat the powder surface and render the particles hydrophobic in nature. The organic pigments are generally various aromatic types including azo, indigoid, triphenylmethane, anthraquinone, and xanthine dyes which are designated as D&C and FD&C blues, browns, greens, oranges, reds, yellows, etc. Organic pigments generally consist of insoluble metallic salts of certified color additives, referred to as the Lakes. Inorganic pigments include iron oxides, ultramarine and chromium or chromium hydroxide colors, and mixtures thereof.

The advantage of the interphase of the emulsion is to provide a stable system to incorporate polyorganosiloxanes with other additional ingredients, such as topical compositions. For example, cosmetic or sunscreen products include one or more polyorganosiloxanes with other additional ingredients within the oil phase. After that, the oil phase is dispersed in an aqueous phase that is free of surfactants and an interphase forms after the neutralization process to achieve and maintain a stable emulsion. The topical composition can also include other ingredients in the aqueous or organic diol medium or oil such as synthetic, natural or modified oils, waxes, esters, fragrances, flavorings, plant extracts, vitamins, proteins and biologically derived agents, sunscreens, particulate powders and pigments, colors, dyes, personal care active agents, healthcare active agents and pharmaceutically active agents. It can also provide a visually transparent or visually translucent appearance by matching the refractive index between the oil phase and aqueous phase based on Snell's law. In one embodiment, any type of glycol (For example: Glycerin) with a refractive index greater than 1.4 can be added to the aqueous phase in order to prepare a transparent or translucent topical composition with the emulsion of the present disclosure. In addition, preservatives can be added such as Phenoxyethanol, DMDM hydantoin, Caprylyl Glycol & Chlorphenesin, 3[(2-Ethylhexyl)oxy]1, 2-propandiol without affecting the stability of the emulsion.

Examples

The following examples are intended to further illustrate certain preferred embodiments of the invention and are not limiting in nature. Those skilled in the art will recognize, or be able to ascertain, using no more than routine experimentation, numerous equivalents to the specific substances and procedures described herein.

Emulsions

Emulsions of polyorganosiloxane with aqueous medium include 2 major phases, an aqueous or anhydrous organic diol phase (AP) and an oil phase (OP). For the emulsion, the OP includes a polyorganosiloxane having one or more hydroxyl groups, e.g., dimethiconol, and one or more polyorganosiloxanes with or without any types of synthetic, natural or modified oils. The AP includes an anionic polymer, e.g. carbomer, in an aqueous or anhydrous organic diol phase.

Emulsions of polyorganosiloxanes with aqueous or anhydrous organic diol medium were created by mixing the OP with the AP. During a neutralization of the mixture of OP and AP, the interphase will be created and then stabilized by the attractive force between the carboxyl and hydroxyl groups with oil droplets formed within an aqueous medium. The interphase (attractive force) is strong enough to stabilize each oil droplet and it is flexible with a self-healing functionality. This means the oil droplets can be dispersed to smaller size with a new interphase until the attractive force no longer stabilizes the system. It also means a small amount of oils (non-polar) can be added into the emulsion and will permeate the interphase and combine with the OP.

In addition, the viscosity of the emulsion is controlled by OP viscosity, types of carbomer, concentration of carbomer and the pH. In general, carbomer in aqueous media often have a pH less than 4.5 and therefore a basic material is used for neutralization, e.g., sodium hydroxide.

The following emulsions were prepared and have an opaque appearance. Glycerin was not used in the present example to achieve refractive index matching between the AP and OP. However, glycerin can be used if translucent or transparent appearance is desirable for a specific application.

The following formulations were prepared according to the following general procedure. Step 1 (Aqueous or anhydrous organic diol phase): Weigh out water or anhydrous organic diol and add carbomer slowly into a vessel. Mix until carbomer is completely dissolved. Step 2 (Oil phase with a continuous neutralization process): Weigh out polysiloxanes and add into a vessel. Mix well until homogenous. Step 3: Add Aqueous or anhydrous organic diol phase into the vessel with the Oil phase and mix well until homogenous. Step 4: Add preservatives into the vessel and mix well until homogenous. Step 5: Add NaOH into the vessel and mix well until homogenous.

Emulsion 1

| Aqueous Phase (AP) | | | |
|---|---|---|---|
| Commercial Name | Supplier | INCI Name | % w/w |
| Water | — | Aqua | 99.01 |
| Tego Carbomer 340FD | EVONIK | Carbomer | 0.99 |
| Total | | | 100 |

| Oil phase(OP)/Neutralization | | | |
|---|---|---|---|
| Commercial Name | Supplier | INCI Name | % w/w |
| CXG-1104 | NUSIL | Dimethicone (and) Dimethicone/Vinyl Dimethicone Crosspolymer | 17.25 |
| CSF-3504 | NUSIL | Dimethicone(and) Dimethiconol | 8.06 |
| Aqueous Phase (AP) | NUSIL | Aqua; Carbomer | 70.84 |
| Microcare PE | THOR | Phenoxyethanol | 1.02 |
| Microcare PTG | THOR | Pentylenglycol | 2.61 |
| Sodium Hydroxide | UNIVAR | Sodium Hydroxyde | 0.22 |
| Total | | | 100 |

The AP contained carbomer and water and the OP/Neutralization contained several polyorganosiloxane, aqueous phase (AP), several preservatives and neutralizing agent such as sodium hydroxide.

The aqueous phase (AP) was prepared with a homogenized mixing between water and carbomer by a single shaft disperser with a low shear blade. The Oil phase (OP)/Neutralization was prepared with a premixed CXG-1104/CSF-3504 blend and AP by a single shaft disperser with a high shear blade. After the mixture was fully mixed, preservatives were added and the composition was neutralized by the neutralizing agent in order to raise the pH and reach the desired viscosity.

The ratio of the 2 solutions is shown in the following table:

| | % w/w |
|---|---|
| AP | 74.69% |
| OP | 25.81% |
| Total | 100% |

After this process, an opaque gel emulsion was obtained with the following composition:

| Final Composition | | | | |
|---|---|---|---|---|
| Commercial Name | Supplier | INCI Name | % w/w | % w/w PHASES |
| AQUEOUS PHASE | | | | |
| Water | / | Aqua | 70.13 | 93.89 |
| Microcare PE | THOR | Phenoxyethanol | 1.02 | 1.37 |
| Microcare PTG | THOR | Pentylenglycol | 2.61 | 3.49 |
| Tego Carbomer 340FD | EVONIK | Carbomer | 0.71 | 0.95 |
| Sodium Hydroxide | UNIVAR | Sodium Hydroxyde | 0.22 | 0.30 |
| Total | | | 74.69 | 100 |
| SILICONE PHASE | | | | |
| CXG-1104 | NUSIL | Dimethicone (and) Dimethicone/Vinyl Dimethicone Crosspolymer | 17.25 | 68.15 |
| CSF-3504 | NUSIL | Dimethicone (and) Dimethiconol | 8.06 | 31.85 |
| Total | | | 25.31 | 100 |
| Total | | | 100.00 | |

Emulsion 2

The following formulations were prepared.

| Aqueous Phase (AP) | | | |
|---|---|---|---|
| Commercial Name | Supplier | INCI Name | % w/w |
| Water | — | Aqua | 99.455 |
| Tego Carbomer 340FD | EVONIK | Carbomer | 0.54 |
| Sodium Hydroxide | UNIVAR | Sodium Hydroxide | 0.005 |
| Total | | | 100 |

| Oil phase(OP)/Neutralization | | | |
|---|---|---|---|
| Commercial Name | Supplier | INCI Name | % w/w |
| CXG-1104 | NUSIL | Dimethicone (and) Dimethicone/Vinyl Dimethicone Crosspolymer | 24.43 |
| CSF-3504 | NUSIL | Dimethicone(and) Dimethiconol | 6.11 |
| Aqueous Phase (AP) | NUSIL | Aqua; Carbomer; Sodium Hydroxyde | 65.14 |
| Microcare PE | THOR | Phenoxyethanol | 0.97 |
| Microcare PTG | THOR | Pentylenglycol | 3.21 |
| Sodium Hydroxide | UNIVAR | Sodium Hydroxide | 0.14 |
| Total | | | 100 |

The AP contained carbomer, water and sodium hydroxide and the OP/Neutralization contained several polyorganosiloxane, aqueous phase (AP), several preservatives and neutralizing agent.

The aqueous phase (AP) was prepared by mixing water and carbomer using a single shaft disperser with a low shear blade. After the carbomer was completely dissolved, sodium hydroxide was added to raise the pH to about 6. This is a pre-neutralized step since the AP is still acidic. The Oil phase (OP)/Neutralization was prepared with a premixed CXG -1104/CSF-3504 blend and AP using a single shaft disperser with a high shear blade. After the mixture was fully mixed, preservatives were added and the composition was neutralized via addition of neutralizing agent in order to raise the pH and reach the desired viscosity.

The ratio of the 2 solutions is shown in the following table:

|  | % w/w |
|---|---|
| AP | 69.46% |
| OP | 30.54% |
| Total | 100% |

After this process, an opaque gel emulsion was obtained with the following composition:

| Final Composition | | | | |
|---|---|---|---|---|
| Commercial Name | Supplier | INCI Name | % w/w | % w/w PHASES |
| AQUEOUS PHASE | | | | |
| Water | / | Aqua | 64.78 | 93.26 |
| Microcare PE | THOR | Phenoxyethanol | 0.97 | 1.40 |
| Microcare PTG | THOR | Pentylenglycol | 3.21 | 4.62 |
| Tego Carbomer 340FD | EVONIK | Carbomer | 0.35 | 0.50 |
| Sodium Hydroxide | UNIVAR | Sodium Hydroxyde | 0.15 | 0.22 |
| Total | | | 69.46 | 100 |
| SILICONE PHASE | | | | |
| CXG-1104 | NUSIL | Dimethicone (and) Dimethicone/Vinyl Dimethicone Crosspolymer | 24.43 | 79.99 |
| CSF-3504 | NUSIL | Dimethicone(and) Dimethiconol | 6.11 | 20.01 |
| Total | | | 30.54 | 100 |
| Total | | | 100.00 | |

Emulsion 3

The following formulations were prepared.

| Aqueous Phase (AP) | | | |
|---|---|---|---|
| Commercial Name | Supplier | INCI Name | % w/w |
| Water | — | Aqua | 99.01 |
| Tego Carbomer 340FD | EVONIK | Carbomer | 0.99 |
| Total | | | 100 |

| Oil phase(OP)/Neutralization | | | |
|---|---|---|---|
| Commercial Name | Supplier | INCI Name | % w/w |
| CSF-3502 | NUSIL | Dimethicone(and) Dimethiconol | 25.31 |
| Aqueous Phase (AP) | NUSIL | Aqua; Carbomer | 70.84 |
| Microcare PE | THOR | Phenoxyethanol | 1.04 |
| Microcare PTG | THOR | Pentylenglycol | 2.59 |
| Sodium Hydroxide | UNIVAR | Sodium Hydroxyde | 0.22 |
| Total | | | 100 |

The AP contained carbomer, water and sodium hydroxide and the OP/Neutralization contained several polyorganosiloxanes, aqueous phase (AP), several preservatives and neutralizing agent.

The aqueous phase (AP) was prepared by mixing water and carbomer using a single shaft disperser with a low shear blade. After the carbomer was completely dissolved, sodium hydroxide was added to raise the pH to about 6. This is a pre-neutralization step since the AP is still acidic. The Oil phase (OP)/Neutralization was prepared with CSF-3502 and AP using a single shaft disperser with a high shear blade. After the mixture was fully mixed, preservatives were added and the composition was neutralized via addition of neutralizing agent in order to raise the pH and reach the desired viscosity.

The ratio of the 2 solutions is shown in the following table:

|  | % w/w |
|---|---|
| AP | 74.69% |
| OP | 25.31% |
| Total | 100% |

After this process, an opaque gel emulsion was obtained with the following composition:

| Final Composition | | | | |
|---|---|---|---|---|
| Commercial Name | Supplier | INCI Name | % w/w | % w/w PHASES |
| AQUEOUS PHASE | | | | |
| Water | / | Aqua | 70.14 | 93.91 |
| Microcare PE | THOR | Phenoxyethanol | 1.04 | 1.39 |
| Microcare PTG | THOR | Pentylenglycol | 2.59 | 3.47 |
| Tego Carbomer 340FD | EVONIK | Carbomer | 0.70 | 0.94 |
| Sodium Hydroxide | UNIVAR | Sodium Hydroxide | 0.22 | 0.29 |
| Total | | | 74.69 | 100 |
| SILICONE PHASE | | | | |
| CSF-3502 | NUSIL | Dimethicone(and) Dimethiconol | 25.31 | 100 |
| Total | | | 25.31 | 100 |
| Total | | | 100.00 | |

Emulsion 4

The following formulations were prepared.

| Aqueous Phase (AP) | | | |
|---|---|---|---|
| Commercial Name | Supplier | INCI Name | % w/w |
| Water | — | Aqua | 99.455 |
| Tego Carbomer 340FD | EVONIK | Carbomer | 0.54 |
| Sodium Hydroxide | UNIVAR | Sodium Hydroxide | 0.005 |
| Total | | | 100 |

| Oil phase(OP)/Neutralization | | | |
|---|---|---|---|
| Commercial Name | Supplier | INCI Name | % w/w |
| CFF-3401 | NUSIL | Trifluoropropyl Dimethicone | 24.43 |
| CSF-3504 | NUSIL | Dimethicone(and) Dimethiconol | 6.11 |
| Aqueous Phase (AP) | NUSIL | Aqua; Carbomer; Sodium Hydroxyde | 65.14 |
| Microcare PE | THOR | Phenoxyethanol | 0.97 |
| Microcare PTG | THOR | Pentylenglycol | 3.26 |
| Sodium Hydroxide | UNIVAR | Sodium Hydroxide | 0.09 |
| Total | | | 100 |

The AP contained carbomer, water and sodium hydroxide and the OP/Neutralization contained several polyorganosiloxanes, aqueous phase (AP), several preservatives and neutralizing agent such as sodium hydroxide.

The aqueous phase (AP) was prepared by mixing water and carbomer using a single shaft disperser with a low shear blade. After the carbomer was completely dissolved, sodium hydroxide was added to raise the pH. This is a pre-neutralization step since the AP is still acidic. The Oil phase (OP)/Neutralization was prepared with a premixed CFF-3401/CSF-3504 blend and AP using a single shaft disperser with a high shear blade. After the mixture was fully mixed, preservatives were added and the composition was neutralized via addition of neutralizing agent in order to raise the pH and reach the desired viscosity.

The ratio between the 2 solutions are shown in the following table:

| | % w/w |
|---|---|
| AP | 69.78% |
| OP | 30.22% |
| Total | 100% |

After this process, an opaque gel emulsion was obtained with the following composition:

| Final Composition | | | | |
|---|---|---|---|---|
| Commercial Name | Supplier | INCI Name | % w/w | % w/w PHASES |
| AQUEOUS PHASE | | | | |
| Water | / | Aqua | 64.79 | 92.84 |
| Microcare PE | THOR | Phenoxyethanol | 0.97 | 1.39 |
| Microcare PTG | THOR | Pentylenglycol | 3.26 | 4.67 |
| Tego Carbomer 340FD | EVONIK | Carbomer | 0.345 | 0.49 |
| Sodium Hydroxide | UNIVAR | Sodium Hydroxyde | 0.415 | 0.61 |
| Total | | | 69.78 | 100 |
| SILICONE PHASE | | | | |
| CFF-3401 | NUSIL | Trifluoropropyl Dimethicone | 24.43 | 80.84 |
| CSF-3504 | NUSIL | Dimethicone(and) Dimethiconol | 6.11 | 19.16 |
| Total | | | 30.22 | 100 |
| Total | | | 100.00 | |

Emulsion 5

The following formulations were prepared.

| Aqueous Phase (AP) | | | |
|---|---|---|---|
| Commercial Name | Supplier | INCI Name | % w/w |
| Water | — | Aqua | 99.01 |
| Tego Carbomer 340FD | EVONIK | Carbomer | 0.99 |
| Total | | | 100 |

| Oil phase(OP)/Neutralization | | | |
|---|---|---|---|
| Commercial Name | Supplier | INCI Name | % w/w |
| CXG-1104 | NUSIL | Dimethicone (and) Dimethicone/Vinyl Dimethicone Crosspolymer | 29.60 |
| CSF-3504 | NUSIL | Dimethicone(and) Dimethiconol | 6.60 |
| Aqueous Phase (AP) | NUSIL | Aqua; Carbomer | 59.10 |
| Butylene Glycol | LOTION CRAFTER | Butylene Glycol | 2.20 |
| Microcare PE | THOR | Phenoxyethanol | 0.56 |
| Sodium Hydroxide @ 10% | NUSIL | Aqua:Sodium Hydroxide | 1.94 |
| Total | | | 100 |

The AP contained carbomer and water and the OP/Neutralization contained several polyorganosiloxanes, aqueous phase (AP), several preservatives and neutralizing agent such as sodium hydroxide.

The aqueous phase (AP) was prepared by mixing water and carbomer using a single shaft disperser with a low shear blade until carbomer was completely dissolved. The Oil phase (OP)/Neutralization was prepared with a premixed CXG-1104/CSF-3504 blend and AP using a single disperser or tri-shaft mixer with a high shear blade. After the mixture was fully mixed, butylene glycol and preservative were added. The composition was neutralized via addition of neutralizing agent in order to raise the pH and reach the desired viscosity.

The ratio between the 2 solutions are shown in the following table:

|  | % w/w |
|---|---|
| AP | 63.80% |
| OP | 36.20% |
| Total | 100% |

After this process, an opaque gel emulsion was obtained with the following composition:

| Final Composition | | | | |
|---|---|---|---|---|
| Commercial Name | Supplier | INCI Name | % w/w | % w/w PHASES |
| AQUEOUS PHASE | | | | |
| Water | / | Aqua | 58.40 | 91.54 |
| Microcare PE | THOR | Phenoxyethanol | 0.56 | 0.88 |
| Butylene Glycol | LOTION CRAFTER | Butylene Glycol | 2.2 | 3.45 |
| Tego Carbomer 340FD | EVONIK | Carbomer | 0.70 | 1.10 |
| Sodium Hydroxide @10% | NUSIL | Aqua:Sodium Hydroxyde | 1.94 | 3.03 |
| Total | | | 63.80 | 100 |
| SILICONE PHASE | | | | |
| CXG-1104 | NUSIL | Dimethicone (and) Dimethicone/Vinyl Dimethicone Crosspolymer | 29.6 | 81.77 |
| CSF-3504 | NUSIL | Dimethicone(and) Dimethiconol | 6.6 | 18.23 |
| Total | | | 36.20 | 100 |
| Total | | | 100.00 | |

Emulsion 6 (Anhydrous)

The following formulations were prepared.

| Anhydrous Phase (AP) | | | |
|---|---|---|---|
| Commercial Name | Supplier | INCI Name | % w/w |
| Zemea Propanediol | LIPSCOMB | Propanediol | 99.01 |
| Tego Carbomer 340FD | EVONIK | Carbomer | 0.99 |
| Total | | | 100 |

| Oil phase(OP)/Neutralization | | | |
|---|---|---|---|
| Commercial Name | Supplier | INCI Name | % w/w |
| CXG-1104 | NUSIL | Dimethicone (and) Dimethicone/Vinyl Dimethicone Crosspolymer | 37.91 |
| CSF-3504 | NUSIL | Dimethicone(and) Dimethiconol | 7.28 |
| Anhydrous Phase (AP) | NUSIL | Propanediol; Carbomer | 54.80 |
| Triethanolamine | | Triethanolamine | 0.01 |
| Total | | | 100 |

The AP contained carbomer and propanediol and the OP/Neutralization contained several polyorganosiloxanes, anhydrous organic diol phase (AP), and neutralizing agent such as triethanolamine.

The anhydrous organic diol phase (AP) was prepared by mixing propanediol and carbomer using a single shaft disperser with a low shear blade until carbomer was completely dissolved. The Oil phase (OP)/Neutralization was prepared with a premixed CXG-1104/CSF -3504 blend and AP using a single disperser or tri-shaft mixer with a high shear blade. After the mixture was fully mixed, the composition was neutralized via addition of neutralizing agent in order to raise the pH and reach the desired viscosity.

The ratio between the 2 solutions are shown in the following table:

|  | % w/w |
|---|---|
| AP | 54.81% |
| OP | 45.19% |
| Total | 100% |

After this process, an opaque gel emulsion was obtained with the following composition:

| Final Composition | | | | |
|---|---|---|---|---|
| Commercial Name | Supplier | INCI Name | % w/w | % w/w PHASES |
| ANHYDROUS PHASE | | | | |
| Zemea Propanediol | LIPSCOMB | Propanediol | 54.27 | 99.01 |
| Tego Carbomer 340FD | EVONIK | Carbomer | 0.54 | 0.99 |
| Total | | | 54.81 | 100 |
| SILICONE PHASE | | | | |
| CXG-1104 | NUSIL | Dimethicone (and) Dimethicone/Vinyl Dimethicone Crosspolymer | 37.91 | 81.77 |
| CSF-3504 | NUSIL | Dimethicone(and) Dimethiconol | 7.28 | 18.23 |
| Total | | | 45.19 | 100 |
| Total | | | 100.00 | |

Topical Compositions

From emulsion 1, 2, 3, 4, 5 or 6, topical cosmetic compositions and topical sunscreen compositions were prepared.

| Topical Composition 1: Refreshing Gel Cream | | | |
|---|---|---|---|
| Phase | Ingredient/Supplier | % | INCI |
| A | Purified Water | 70.5 | Aqua |
|  | Carbopol Ultrez 21 Polymer | 0.5 | Acrylates/C10-30 Alkyl Acrylate Crosspolymer |
|  | Glycerin | 5.5 | Glycerin |
|  | Butylene Glycol | 5.5 | Butylene Glycol |
| B | Emulsion 1 | 12.1 | Aqua (and) Dimethicone/ Vinyl Dimethicone Crosspolymer (and) Dimethicone (and) Dimethiconol (and) |

Topical Composition 1: Refreshing Gel Cream (continued)

| Phase | Ingredient/Supplier | % | INCI |
|---|---|---|---|
|  |  |  | Pentylene Glycol (and) (and) Phenoxyethanol (and) Carbomer (and) Sodium Hydroxide |
| C | Triethanolamine (TEA) | 0.7 | Triethanolamine |
| D | — | 0.5 | Alcohol Denat. |
|  | Sodium Hyaluronate (1%) | 2.0 | Sodium Hyaluronate |
| E | FD&C Blue No1 soln | q.s. | CI 42091 (0.1% sol.) |
|  | Microcare PE/THOR | 0.7 | Phenoxyethanol |
|  | Microcare PTG/THOR | 2.0 | Pentylene Glycol |
|  | Perfume (Ocean Breeze) | q.s. | Perfume |

The process for preparation of the topical composition included preparing an aqueous medium including the carbomer, water, glycerin, butylene glycol as Phase A, then adding Phase A to Phase B while mixing with medium shear until homogeneous then neutralizing with Phase C triethanolamine (TEA). Mixing was continued with medium shear until the emulsion was formed. Phase D was added to combined Phase ABC with medium shear then Phase E was added to combine Phase ABCD with medium shear mixing until homogeneous.

Topical Composition 2: SPF Moisturizing Lotion for Facial

| Phase | Ingredient/Supplier | % | INCI |
|---|---|---|---|
| A | Octinozate//PARSOL MCX | 3.1 | Ethylhexyl methoxycinnamate |
|  | Avobenzone/PARSOL 1789 | 1.5 | Butyl methoxydibenzoylmethane |
|  | Protachem GMS-165 | 4.1 | Glyceryl sterate (and)PEG 100 sterate |
|  | Shea Butter (Refined) | 1.0 | *Butyrospermum parkii* |
|  | PLY-9532-40 | 3.1 | Stearyl dimethicone |
|  | Crodacol C70-PA-(MH)/Croda | 1.0 | Cetyl alcohol |
|  | ESP Organic Sunflower Oil-Hi Oleic/Earth Supplied Products | 4.1 | *Helianthus Annus* (Sunflower) Seed Oil |
|  | Pelemol In-2 | 3.1 | Isononyl isononanoate |
|  | Lonzest DC M181/LONZA | 8.2 | Dicaprylyl carbonate |
|  | Mikrokill COS/LONZA | 0.8 | Phenoxyethanol (and) Chlorphenesin (and) Caprylyl Glycol |
| B | Emulsion 1 | 22.6 | Aqua (and) Dimethicone/Vinyl Dimethicone Crosspolymer (and) Dimethicone (and) Dimethiconol (and) Pentylene Glycol (and) (and) Phenoxyethanol (and) Carbomer (and) Sodium Hydroxide |
|  | Glycerin | 2.1 | Glycerin |
|  | Purified water | 41.1 | Aqua |
| C | Sepigel 305/Seppic | 4.2 | Polyacrylamide (and) C13-14 Isoparaffin (and) Laureth-7 |

The process for preparation of the topical composition included mixing and heating the first two ingredients from Phase A to 60 C while stirring continuously. After the first two ingredients mixed, the remaining ingredients from Phase A were slowly added until homogenous. Phase B ingredients were mixed and added to Phase A while mixing at 800 rpm. Phase C ingredients were added to the mixture with the composition at room temp and mixing was continued until the moisturizer was homogenous.

Topical Composition 3: Anti-Aging Night Cream

| Phase | Ingredient/Supplier | % | INCI |
|---|---|---|---|
| A | Water | 29.5 | Water |
|  | Emulsion 4 | 37.3 | Aqua (and) Trifluoropropyl Dimethicone (and) Dimethicone (and) Dimethiconol (and) Pentylene Glycol (and) (and) Phenoxyethanol (and) Carbomer (and) Sodium Hydroxide |
|  | — | 2.5 | Propylene Glycol |
| B | Duraquench IQ/Croda | 6.2 | Cetyl Alcohol (and) Isostearyl Isostearate (and) Potassium Cetyl Phosphate (and) Cetyl Behenate (and) Behenic Acid |
|  | Klearol/Sonneborn | 1.2 | White mineral oil |
|  | NaturaSoft Shea/Natura-Tec | 1.2 | Shea butter |
|  | Crodacol C90/Croda | 1.2 | Cetyl Alcohol |
|  | Neobee M5/Stepan | 3.7 | Caprylic/Capric Triglyceride |
|  | Glucate SS/Lubrizol | 3.1 | Methyl Glucose Sesquistearate |
|  | Glucamate SSE-20/Lubrizol | 0.6 | PEG-20 Methyl Glucose Sesquistearate |
|  | — | 10 | Isopropyl Myristate |
| C | Gatuline RC Bio | 0.9 | Water (and) *Fagus Sylvatica* Bud Extract |
|  | Actifirm AGE | 1.9 | Dipropylene Glycol (and) *Centella Asiatica* Extract (and) *Echinacea Angustifolia* Leaf Extract (and) *Rosmarinus Officinalis* (Rosemary) Leaf Extract (and) *Ganoderma Lucidum* (Mushroom)Extract (and) AD Alcohol 40-B |
| D | Euxyl PE9010 | 0.5 | Phenoxyethanol (and) Ethylhexlglycerin |
|  | Rose Noire | q.s. | Perfume |

The process for preparing the topical composition included heating Phase A ingredients at 70° C. while mixing. Phase B ingredients were heated at 70° C. while gently mixing until completely melted. Phase A was added to Phase B while mixing with rotor stator device. Mixing was continued with medium shear device until the emulsion is formed. Phase C was added to the combined Phases AB when T<40° C. and mixed until homogenous. Phase D was added to Phase ABC with continuous mixing until the cream was homogeneous.

Topical Composition 4: Moisturizing Lotion for Men

| Phase | Ingredient/Supplier | % | INCI |
|---|---|---|---|
| A | CSF-3504/NuSil | 3.1 | Dimethicone (and) Dimethiconol |
|  | PLY-9532-40/NuSil | 2.1 | Stearyl dimethicone |
|  | Shea Butter (Refined)/Rita | 2.1 | *Butyrospermum parkii* |
|  | HALLSTAR TA-1618/Hallstar | 2.1 | Cetearyl Alochol |
|  | Glyceryl Stearate/Classic Fine Ing. | 1.6 | Glyceryl Stearate |
|  | Olive Oil/Biochemica | 1.0 | Olive Oil |
|  | Ariacel 165/Croda | 2.6 | Glyceryl Stearate (and) PEG 100 Stearate |
|  | Neobee M5/Stepan | 5.2 | Caprylic/Capric Triglyceride |
|  | Emulsion 1 | 33 | Aqua (and) Dimethicone/Vinyl Dimethicone Crosspolymer (and) Dimethicone (and) Dimethiconol (and) Pentylene Glycol (and) (and) Phenoxyethanol (and) Carbomer (and) Sodium Hydroxide |

Topical Composition 4: Moisturizing Lotion for Men

| Phase | Ingredient/Supplier | % | INCI |
|---|---|---|---|
| B | — | 3.1 | Glycerin |
| | Propylene Glycol/Spectrum | 2.1 | Propylene Glycol |
| | — | 0.2 | Xanthan Gum |
| | Purified Water | 40.5 | Aqua |
| C | Glydant 2000/Lonza | 0.2 | DMDM Hydantoin |
| | Vitamin E Acetate/BASF | 0.6 | dl-alpha-tocopherol acetate |
| | D-Panthenol 50P/BASF | 0.5 | Pantenol 50P |

The process for preparing the topical composition included heating Phase A ingredients at 60° C. while mixing. Phase B ingredients were heated at 60° C. while gently mixing until completely melted. Phase A was added to Phase B while mixing with rotor stator device. Mixing was continued with medium shear device until the composition was homogenous. Phase C was added to the combined Phases AB when T<45° C. and mixing was continued until the lotion was homogeneous.

Topical Composition 5: Anti-Aging Day Cream

| Phase | Ingredient/Supplier | % | INCI |
|---|---|---|---|
| A | Octinoxate//PARSOL MCX | 4.3 | Ethylhexyl methoxycinnamate |
| | Neoheliopan 303/Symise | 2.7 | Octocrylene |
| | Revit Elix/Croda | 3.3 | *Echium Plantadineum* Seed Oil |
| | Crodamol AB-LQ(MH)/Croda | 3.3 | C12-15 Alkyl Benzoate |
| | Duraquench IQ/Croda | 7.1 | Cetyl Alcohol (and) Isostearyl Isostearate (and) Potassium Cetyl Phosphate (and) Cetyl Behenate (and) Behenic Acid |
| | Emulium Delta/Gattefose | 3.3 | Cetyl Alcohol (and) Glyceryl Stearate (and)PEG-75 Stearate (and) Ceteth-20 (and) Steareth-20 |
| B | Emulsion 1 | 43.4 | Aqua (and) Dimethicone/Vinyl Dimethicone Crosspolymer (and) Dimethicone (and) Dimethiconol (and) Pentylene Glycol (and) (and) Phenoxyethanol (and) Carbomer (and) Sodium Hydroxide |
| | Purified Water | 32.6 | Aqua |
| C | Fleuri Frais/MLW | q.s. | Perfume |

The process for the topical composition included mixing and heating the first three ingredients from Phase A to 70 C while stirring continuously. After the first three ingredients were mixed, remaining ingredients from Phase A were slowly added until homogenous. Phase B ingredients were pre-mixed and added to Phase A while mixing at 700 rpm. Phase C was added to the combined Phases AB when T<45° C. and mixing was continued until the cream was homogeneous.

Topical Composition 6: Butter Cream

| Phase | Ingredient/Supplier | % | INCI |
|---|---|---|---|
| A | Crodacol C70-PA-(MH)/Croda | 3.7 | Cetyl alcohol |
| | DL-Orange Butter/Deveraux Specialties | 1.9 | DL-Orange Butter |
| | CoCoa Butter (Deodorized)/HallStar | 3.7 | CoCoa Butter |
| | Shea Butter (Refined)/Rita | 3.7 | *Butyrospermum parkii* |
| B | Purified Water | 69.9 | Aqua |
| | Emulsion 5 | 9.5 | Aqua (and) Dimethicone (and) Dimethicone/Vinyl Dimethicone Crosspolymer (and) Dimethiconol (and) Butyl Glycol (and) Carbomer(and) Phenoxyethanol(and) Sodium Hydroxide |
| | Glycerin | 4.7 | Glycerin |
| C | Sepigel 305/Seppic | 2.9 | Polyacrylamide (and) C13-14 Isoparaffin (and) Laureth-7 |
| | Microcare PE/THOR | 0.3 | Phenoxyethanol |

The process for the topical composition included mixing and heating the water from Phase A was slowly added to 60 C while stirring continuously. At 60 C, remaining ingredients from Phase A until homogenous. Phase B ingredients were added to Phase A while mixing at 700 rpm. Phase C was added to the combined Phases AB when T<45° C. and mixing was continued until the cream was homogeneous.

Topical Composition 7: Simple Serum

| Phase | Ingredient/Supplier | % | INCI |
|---|---|---|---|
| A | Speigel EG/Seppic | 2.3 | Sodium Acrylate/Acryloydimethyl Taurate Copolymer (and) Isohexadecane (and) Polysorbate 80 |
| | Emulsion 1 | 40 | Aqua (and) Dimethicone/Vinyl Dimethicone Crosspolymer (and) Dimethicone (and) Dimethiconol (and) Pentylene Glycol (and) (and) Phenoxyethanol (and) Carbomer (and) Sodium Hydroxide |
| | Purified Water | 11.1 | Aqua |
| | Propylene Glycol/Spectrum | 45.7 | Propylene Glycol |
| B | Euxyl PE 9010 | 0.9 | Phenoxyethanol (and) Ethylhexlglycerin |
| | Arancia Di CapriS1368768 | q.s. | Perfume |

The process for the topical composition included mixing Phase A ingredients at 1000 rpm until homogenous. Phase B ingredients were added to Phase A while mixing at 1000 rpm until the serum was homogeneous.

Topical Composition 8: Rejuvenating Serum

| Phase | Ingredient/Supplier | % | INCI |
|---|---|---|---|
| A | Purified Water | 42.4 | Aqua |
| | Carbopol Ultrez 30 Polymer | 0.2 | Carbomer |
| B | Emulsion 1 | 10.9 | Aqua (and) Dimethicone/Vinyl Dimethicone Crosspolymer (and) Dimethicone (and) Dimethiconol (and) Pentylene Glycol (and) (and) Phenoxyethanol (and) Carbomer (and) Sodium Hydroxide |

-continued

Topical Composition 8: Rejuvenating Serum

| Phase | Ingredient/Supplier | % | INCI |
|---|---|---|---|
|  | Glycerin | 42.1 | Glycerin |
|  | Actiphte Cucumber | 2.2 | *Cucumis Sativus* fruit Extract |
|  | Sodium Hyaluronic Acid 1% PHE | 2.2 |  |
|  | Arancia Di CapriS1368768 | q.s. | Perfume |
| C | Sodium Hydroxide | q.s. | Sodium Hydroxide |

The process for the topical composition included preparing an aqueous medium including the carbomer and water as Phase A. Phase A was added to Phase B while mixing with medium shear until homogeneous then neutralized with Phase C Sodium Hydroxide. Mixing was continued with medium shear device until the emulsion was formed.

Topical Composition 9: Moisturizing Hydro Gel

| Phase | Ingredient/Supplier | % | INCI |
|---|---|---|---|
| A | Purified Water | 71.5 | Aqua |
|  | Propylene Glycol/Spectrum | 1.2 | Propylene Glycol |
|  | Denatured Alcohol/BDH | 4.9 | Alcohol Denat. |
|  | Sodium Hyaluronic Acid 1% PHE/Caribbean Natural Product | 1.2 | Sodium Hyaluronic Acid 1% PHE |
|  | Emulsion 3 | 14.0 | Aqua (and) Dimethicone (and) Dimethiconol (and) Pentylene Glycol (and) (and) Phenoxyethanol (and) Carbomer (and) Sodium Hydroxide |
| B | Lonzest DC M181/LONZA | 3.0 | Dicaprylyl carbonate |
|  | Simulgel INS 100/Seppic | 3.6 | Hydroxyethyl Acrylate/Sodium Acryloydimethyl Taurate Copolymer(and) Isohexadecane (and) Polysorbate 60 |
|  | Neobee M5/Stepan | 0.6 | Caprylic/Capric Triglyceride |
| C | Fit & Healthty/Luzi | q.s. | Perfume |
|  | FDC Blu no 1 | q.s. | CI 42091 (0.1% sol.) |

The process for the topical composition included preparing mixing Phase A ingredients at 1000 rpm until homogenous. Phase B ingredients were added to Phase A while mixing at 1000 rpm. Phase C ingredients were added to the combined Phase AB and mixing continued until the hydrogel was homogenous.

Topical Composition 10: Serum Gel

| Phase | Ingredient/Supplier | % | INCI |
|---|---|---|---|
| A | Glycerin/UNIVAR | 44.44 | Glycerin |
|  | Purified Water/A. G. LAYNE | 33.33 | Aqua |
|  | Emulsion 5 | 22.23 | Aqua (and) Dimethicone (and) Dimethicone/Vinyl Dimethicone Crosspolymer (and) Dimethiconol (and) Butyl Glycol (and) Carbomer(and) Phenoxyethanol(and) Sodium Hydroxide |
|  | Kiwi Fragrance 2 | q.s. | Perfume |

The process for the topical composition included mixing CSG-1001 with water and glycerin with spatulas or any medium shear device until homogenous then adding perfume for fragrance.

Topical Composition 11: Hydration Surge

| Phase | Ingredient /Supplier | % | INCI |
|---|---|---|---|
| A | Purified Water | 65.80 | Aqua |
|  | Glycerin/UNIVAR | 5.6 | Glycerin |
|  | Sodium Hyaluronate @ 1% Soln/ Caribbean Natural Product | 5.6 | Sodium Hyaluronate |
|  | Emulsion 5 | 11.1 | Aqua (and) Dimethicone (and) Dimethicone/Vinyl Dimethicone Crosspolymer (and) Dimethiconol (and) Butyl Glycol (and) Carbomer(and) Phenoxyethanol(and) Sodium Hydroxide |
|  | Butylene Glycol/LotionCrafter | 5.6 | Butylene Glycol |
| B | Simulgel INS 100/Seppic | 2.8 | Hydroxyethyl Acrylate/Sodium Acryloydimethyl Taurate Copolymer(and) Isohexadecane (and) Polysorbate 60 |
| C | Microcare PE/Thor | 0.7 | Phenoxethanol |
|  | FD&C Red 7 | q.s. | CI07004 (0.1% sol.) |
|  | Fleuri Frais/MLW | q.s. | Perfume |

The process for the topical composition included preparing mixing Phase A ingredients at 1000 rpm until homogenous. Phase B ingredients were added to Phase A while mixing at 1000 rpm. Phase C ingredients were added to the combined Phase AB and mixing continued until the hydrogel was homogenous.

Only the preferred embodiment of the present invention and examples of its versatility are shown and described in the present disclosure. It is to be understood that the present invention is capable of use in various other combinations and environments and is capable of changes or modifications within the scope of the inventive concept as expressed herein. Thus, for example, those skilled in the art will recognize, or be able to ascertain, using no more than routine experimentation, numerous equivalents to the specific substances, procedures and arrangements described herein. Such equivalents are considered to be within the scope of this invention, and are covered by the following claims.

What is claimed is:

1. A silicone emulsion comprising a dispersed oil phase comprising a hydroxyl terminated or hydroxyalkyl terminated polyorganosiloxane in a continuous phase comprising an aqueous or organic diol medium including an anionic polymer having carboxyl groups-, wherein the silicone emulsion is free of a surfactant or an emulsifier, and wherein stability of said silicone emulsion is achieved by hydrogen bonding interactions and steric stabilization between the hydroxyl terminated or hydroxyalkyl terminated polyorganosiloxane and the anionic polymer having carboxyl groups, wherein said silicone emulsion is free of fillers.

2. The emulsion according to claim 1, wherein the anionic polymer is a polyacrylic acid polymer.

3. The emulsion according to claim 1, wherein the oil phase further comprises one or more organic based oil, hydrocarbon based oil, or an oil containing silicon atoms.

4. The emulsion according to claim 1, wherein the emulsion further comprises one or more active agents.

5. The emulsion according to claim 1, wherein the emulsion has a viscosity greater than about 10,000 centipoise (cP).

6. The emulsion according to claim 1, wherein the emulsion is included in a topical cosmetic composition.

7. The emulsion according to claim 4, wherein one or more active agents includes a water soluble or oil soluble pharmaceutical active.

8. The emulsion according to claim 7, wherein the water soluble or oil soluble pharmaceutical active is selected from the group consisting of hydrocortisone, ketoprofen, timolol, pilocarpine, adriamycin, mitomycin C, morphine, hydromorphone, diltiazem, theophylline, doxorubicin, daunorubicin, heparin, penicillin G, carbenicillin, cephalothin, cefoxitin, cefotaxime, 5-fluorouracil, cytarabine, 6-azauridine, 6-thioguanine, vinblastine, vincristine, bleomycin sulfate, aurothioglucose, suramin, mebendazole clonidine, scopolamine, propranolol, phenylpropanolamine hydrochloride, ouabain, atropine, haloperidol, isosorbide, nitroglycerin, ibuprofen, ubiquinones, indomethacin, prostaglandins, naproxen, salbutamol, guanabenz, labetalol, pheniramine, metrifonate, and steroids.

9. The emulsion according to claim 4, wherein one or more active agents includes vitamins, vitamin derivatives, or pro-vitamins.

10. The emulsion according to claim 9, wherein the vitamins, vitamin derivatives, or pro-vitamins are selected from the group consisting of Vitamin A1, retinol, $C_2$-$C_{18}$ esters of retinol, vitamin E, tocopherol, esters of vitamin E, trans-retinol, 1,3-cis-retinol, 11-cis-retinol, 9-cis-retinol, 3,4-didehydro-retinol, Vitamin C and its derivatives, Vitamin B1, Vitamin B2, Pro Vitamin B5, panthenol, Vitamin B6, Vitamin B12, niacin, folic acid, biotin, pantothenic acid, ascorbyl dipalmitate, ascorbyl methylsilanol pectinate, ascorbyl palmitate, ascorbyl stearate, ascorbyl glucocide, sodium ascorbyl phosphate, sodium ascorbate, disodium ascorbyl sulfate, and potassium (ascorbyl/tocopheryl) phosphate.

11. The emulsion according to claim 4, wherein one or more active agents includes proteins or enzymes.

12. The emulsion according to claim 4, wherein one or more active agents includes a sunscreen ingredient.

13. The emulsion according to claim 1, wherein the hydroxyl terminated polyorganosiloxane is dimethiconol.

14. The emulsion according to claim 1, wherein the silicone emulsion is free of amodimethicone.

* * * * *